United States Patent [19]

Tanaka et al.

[11] Patent Number: 5,730,702
[45] Date of Patent: Mar. 24, 1998

[54] ENDOSCOPIC ILLUMINATION LIGHT CONTROL

[75] Inventors: Toshizumi Tanaka; Kazuhiro Yamanaka, both of Omiya, Japan

[73] Assignee: Fuji Photo Optical Co., Ltd., Omiya, Japan

[21] Appl. No.: 895,868

[22] Filed: Jul. 17, 1997

Related U.S. Application Data

[63] Continuation of Ser. No. 473,944, Jun. 7, 1995, abandoned.

[30] Foreign Application Priority Data

Jun. 16, 1994 [JP] Japan .................................. 6-156425

[51] Int. Cl.$^6$ .................................................. A61B 1/07
[52] U.S. Cl. ...................... 600/180; 600/103; 600/118; 600/178; 600/182; 362/276
[58] Field of Search ..................... 600/103, 108, 600/117, 118, 152, 178, 180–182; 606/10–12, 15, 16; 362/32, 276; 128/634, 665

[56] References Cited

U.S. PATENT DOCUMENTS

| 4,543,477 | 9/1985 | Dei et al. ........................... 606/16 X |
| 5,219,345 | 6/1993 | Potter ................................. 606/15 |
| 5,505,687 | 4/1996 | Walther et al. .................... 600/182 |

Primary Examiner—Richard J. Apley
Assistant Examiner—John Mulcahy
Attorney, Agent, or Firm—Oblon, Spivak, McClelland, Maier & Neustadt, P.C.

[57] ABSTRACT

An illumination light control for an endoscope having an illumination window side by side with an observation window at the distal end of a catheter-like flexible insertion rod member of the endoscope, along with a light guide extended through the insertion rod member down to the illumination window to irradiate a subject under observation through the observation window. A window blockage sensor is located within the illumination window to detect existence of an intracavitary wall or other blocking obstacles in abnormal nearness of the illumination window by way of light reflection from the blocking obstacle.

5 Claims, 6 Drawing Sheets

F I G. 2
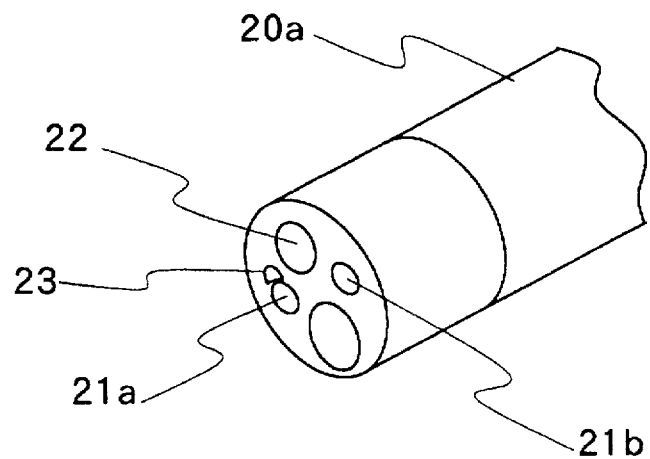
F I g. 5
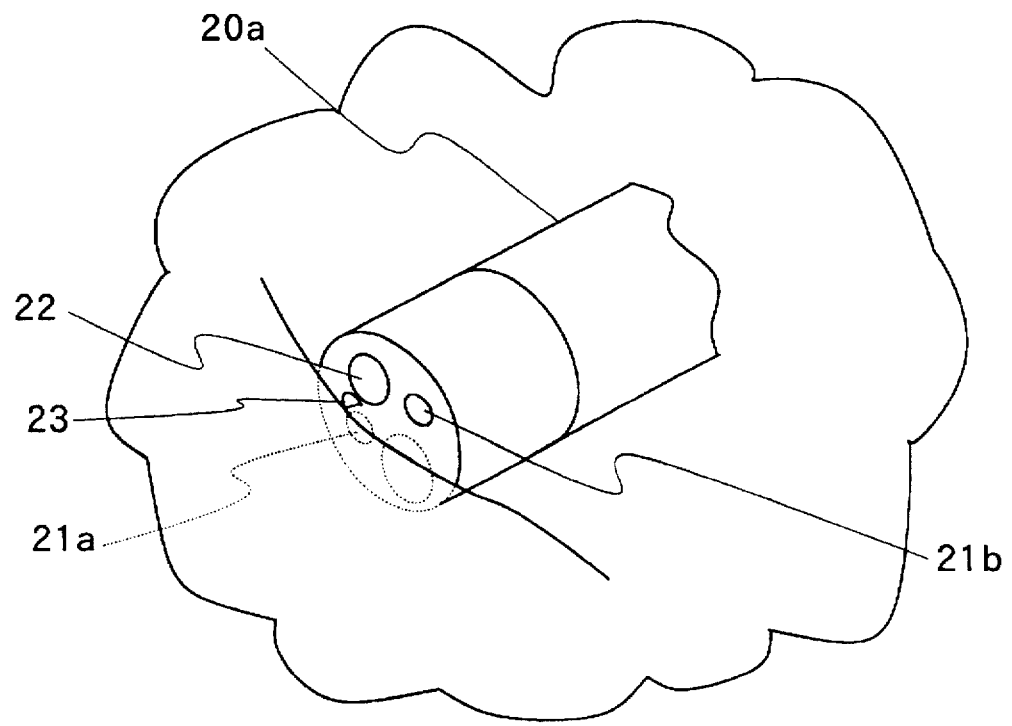

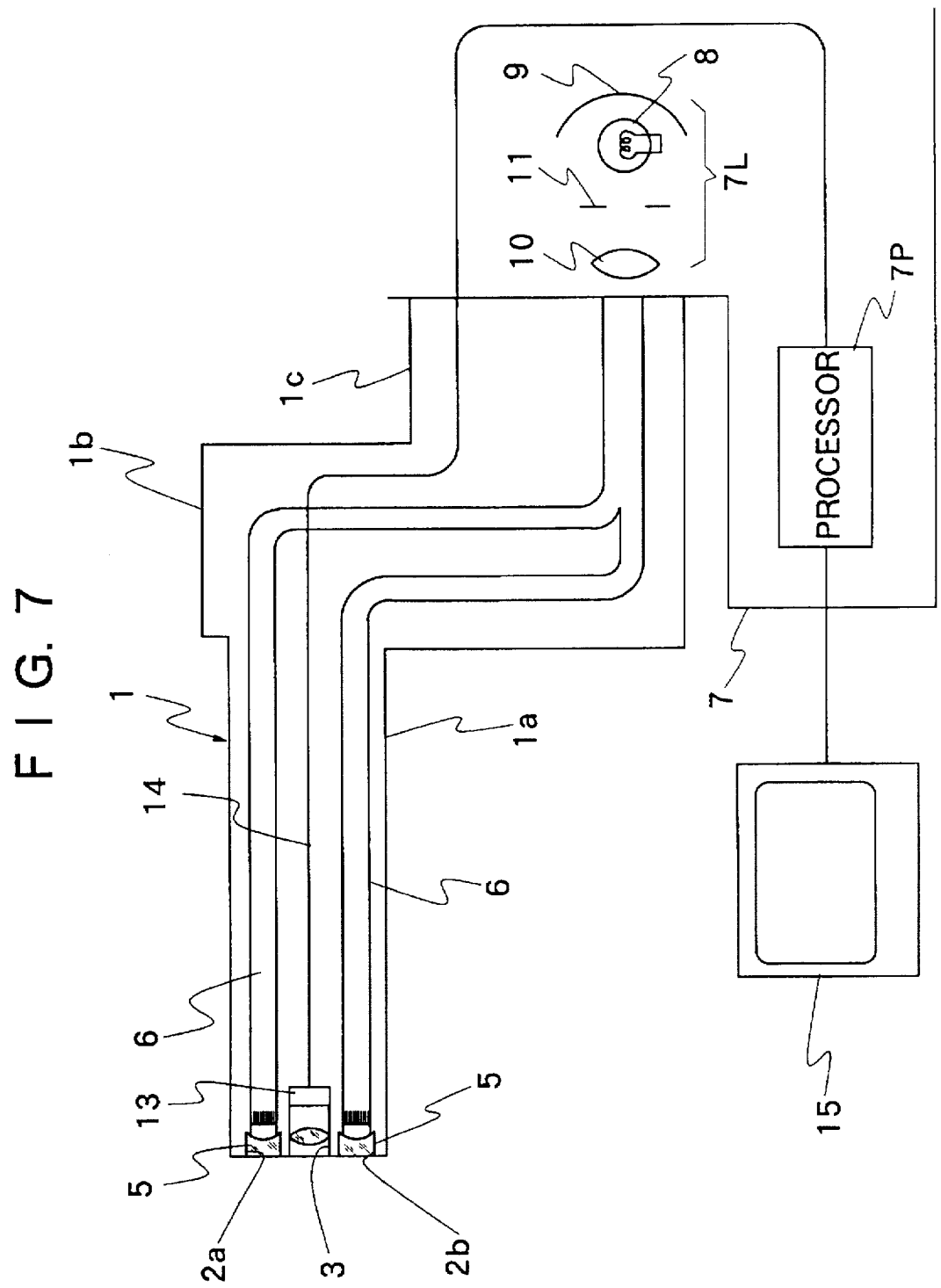

ENDOSCOPIC ILLUMINATION LIGHT CONTROL

This application is a Continuation of application Ser. No. 08/473,944, filed on Jun. 7, 1995, now abandoned.

BACKGROUND OF THE INVENTION

1. Field of the Art

This invention relates to endoscopic illumination light controls, and more particularly to an endoscopic illumination light control with a sensor means at an illumination window at the distal end of a catheter-like insertion rod of an endoscope to prevent the illumination window from being continuedly blocked by an intracavitary wall portion or similar obstacles during use of the endoscope.

2. Prior Art

FIG. 7 shows general arrangements of illumination and observation systems of a conventional electronic endoscope, in which indicated at 1 is an endoscope having a couple of illumination windows 2a and 2b (hereinafter referred to collectively as "illumination window 2" whenever the same description applies commonly to both) at the distal end of a flexible catheter-like insertion rod 1a side by side with an observation window 3.

The endoscope includes in its illumination system an illumination lens 5 which is fitted in the illumination window 2, and a light guide 6 in the form of a bundle of a multitude of ultra fine fiber optics. The light guide 6 is extended through the insertion rod 1a and a manipulating control section 1b on the main body of the endoscope 1, and led through a flexible light guide cable 1c which is detachably connectible to a light source/processor assembly unit 7 with an illumination lamp 8 in its light source section 7L. Light rays from the illumination lamp 8 are directed toward a light incident face at the end of the light guide 6 by a concave reflector mirror 9 and a condensing lens 10. Located between the condensing lens 10 and the illumination lamp 8 is a light volume member 11 thereby to adjust the volume of illumination light to be supplied to the input end of the light guide 6.

On the other hand, the observation system of the endoscope includes an objective lens 12 which is fitted in the observation window 3, and a solid-state image sensor 13 such as CCD or the like which is located at the focus of the objective lens 12. Similarly to the light guide 6, a signal cable 14 from the solid-state image sensor 13 is extended through the insertion rod 1a and the flexible light guide cable 1c via the manipulating control section 1b of the endoscope. When the flexible light guide cable 1c is connected to the light source/processor assembly unit 7, the signal cable 14 is electrically connected to a processor 7P thereby to convert the output signals of the solid-state image sensor 13 into video signals by predetermined known signal processing operations. The resulting video signals are transferred to a monitor 15 to display on its viewing screen video images of an intracavitary portion under observation. The processor 7P is usually adapted to detect the brightness of video images from the output signal level of the solid-state image sensor 13, controlling the light volume member 11 on the basis of the detected brightness of video images for the purpose of adjusting the input light volume of the light guide 6 to a level which can ensure sufficient luminosity of video images on the viewing screen of the monitor 15 while preventing blooming, smear or other image degradations as caused by saturation of the solid-state image sensor 13.

The light guide 6 of the illumination system should be of a relatively small diameter because it has to be passed through the catheter-like insertion rod 1a to be introduced into an alimentary canal or other intracavitary portions of a patient. Besides, it should be able to illuminate an intracavitary region under observation over as broad a range as possible. In order to meet these requirements, arrangements are usually made to transmit an extremely large quantity of illumination light through the light guide 6 and to diffuse the light rays over a wide range through the illumination lens 5. Therefore, normally a heat-absorbing filter is inserted in the light path at a position upstream of the light incident face at the input end of the light guide 6 thereby to absorb heat to some extent. However, since a filter of this sort is not capable of absorbing heat completely, it is often the case that the light beams incident on the input end of the light guide still contain a large quantity of heat.

While the insertion rod 1a of the endoscope 1 is placed in a certain intracavitary region for an endoscopic observation, the distal end face of the insertion rod 1a is often abutted against an intracavitary wall in such a way that one of the observation windows, for example, the illumination window 2a is blocked by the abutting intracavitary wall while the other illumination window 2b remains unblocked and open immediately on the front side thereof. Under such circumstances, the intracavitary portion under observation is irradiated with light rays from the unblocked illumination window 2b only. In response to a resulting drop in the illumination light level, the processor 7P produces a signal to drive the light volume member 11 toward a full-open position for quantitatively increasing the illumination light to be fed to the light guide 6. As a consequence, illumination light of an intensified level is transmitted to the illumination windows, including the illumination window 2a which is blocked by the intracavitary wall, and impinged on a particular spot on the blocking intracavitary wall before being diffused over a broader range by the illumination lens, despite the risk of causing thermal burns or similar damages to the irradiated spot.

SUMMARY OF THE INVENTION

In view of the foregoing situations, it is a primary object of the present invention to provide an endoscopic illumination light control capable of easily detecting the existence of an intracavitary wall or other obstacles blocking part of or entire areas of an illumination window at the distal end of an insertion rod member of an endoscope.

In accordance with the present invention, the above-stated objective is achieved by the provision of an illumination light control for an endoscope having a light guide passed through an insertion rod member of the endoscope to transmit light rays to an illumination window at the distal end of the insertion rod, characterized in that the illumination light control comprises a window blockage sensor unit adapted to detect existence of a blocking obstacle immediately on the front side of the illumination window by way of light reflections from the blocking obstacle.

BRIEF DESCRIPTION OF THE DRAWINGS

The above and other objects, features and advantages of the invention will become apparent from the following particular description of the invention, taken in conjunction with the accompanying drawings which show by way of example a preferred embodiment of the invention and in which:

FIG. 2 is an outer view of a distal end portion of a catheter-like insertion rod member of the endoscope;

FIG. 5 is a schematic view of a tip end portion of the insertion rod member placed in an intracavitary region for an endoscopic observation;

FIG. 7 is a view similar to FIG. 1 but showing the general layout of a conventional endoscopic control system.

DESCRIPTION OF PREFERRED EMBODIMENTS

Hereafter, the invention is described more particularly by way of its preferred embodiments with reference to the drawings.

Figure 1:
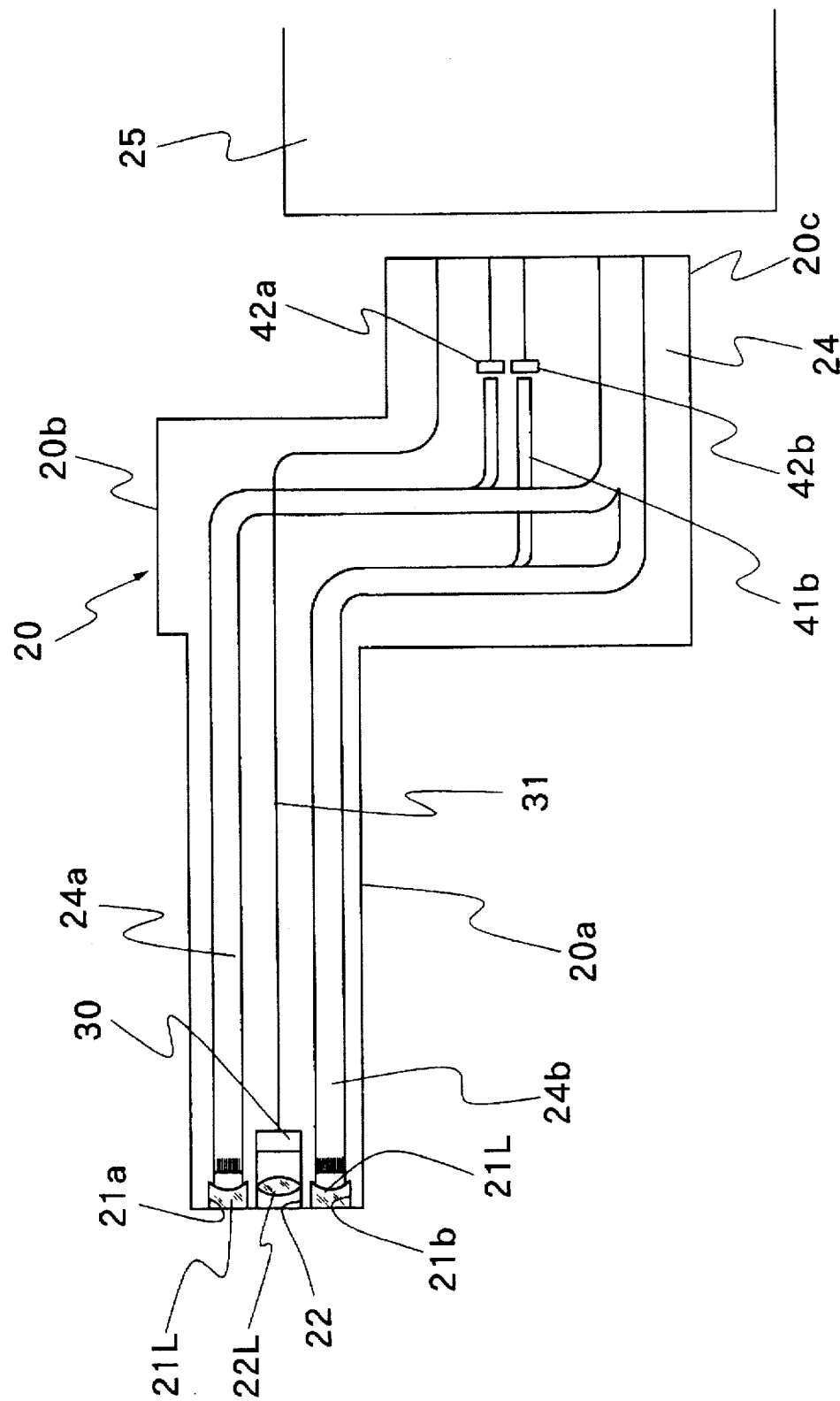
FIG. 1 is a diagrammatic illustration, showing the general layout of an endoscopic control system incorporating an illumination light control according to the present invention.

Referring first to FIG. 1, indicated at 20 is an endoscope which is largely constituted by a flexible catheter-like insertion rod member 20a, a main body or manipulating control section 20b which is connected to the proximal end of the insertion rod member 20a, and a flexible light guide cable 20c which is extended out from the control section 20b for connection to a light source which will be described hereinlater. Provided on the distal end face of the insertion rod member 20a are a couple of illumination windows 21a and 21b (hereinafter collectively referred to as "illumination window 21" whenever the same description applies commonly to both) and an observation window 22, which are fitted with illumination lenses 21L and an objective lens 22L, respectively. The insertion rod member 20a which is designed to be introduced into an intracavitary portion is provided with a washing nozzle 23 which spouts a cleaning fluid to wash contaminants off the observation window 22 whenever necessary.

Figure 3:
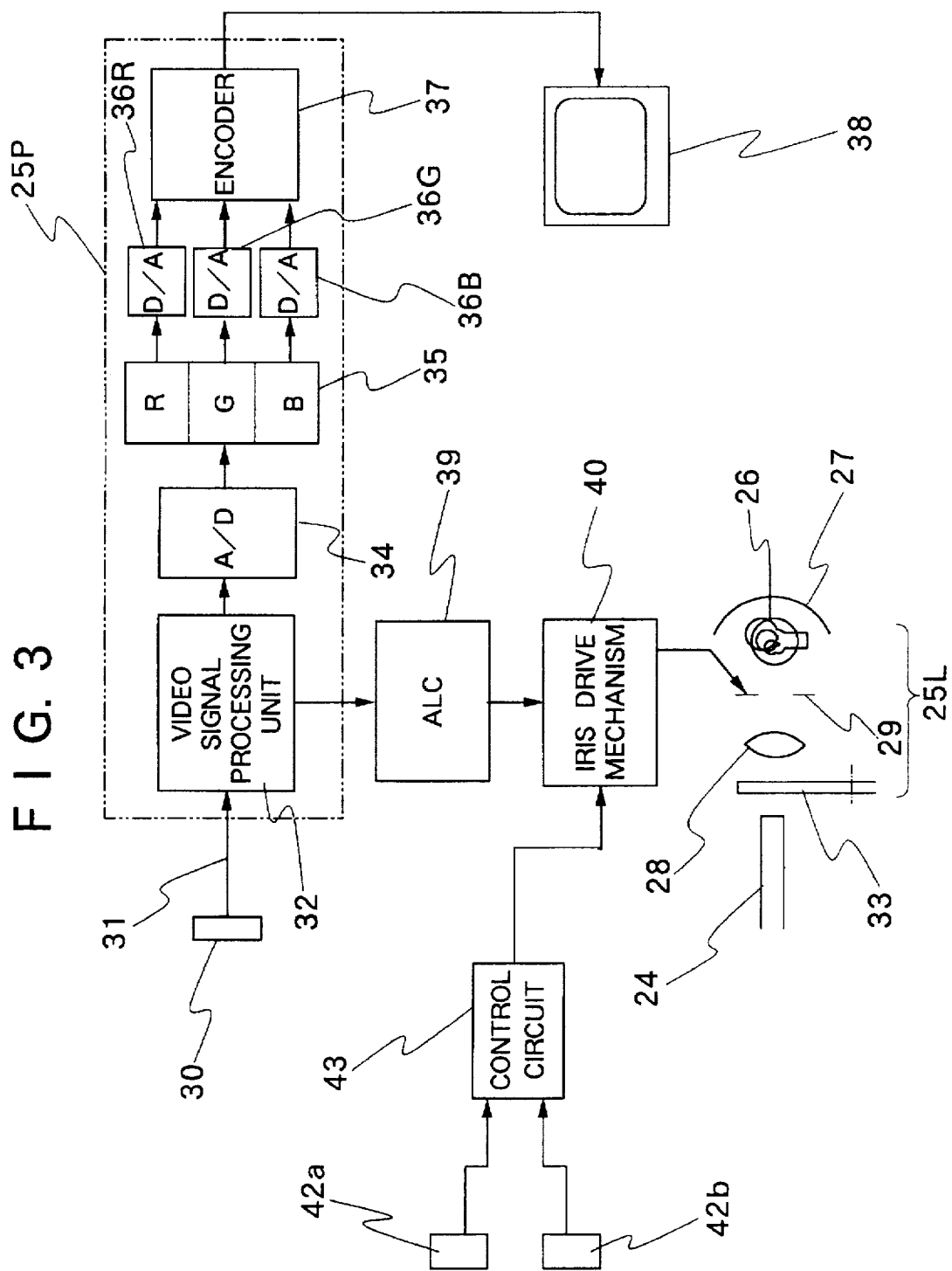
FIG. 3 is a circuit diagram of a processor.

The endoscope 20 includes in its illumination system a couple of light guides 24a and 24b (hereinafter collectively represented by a reference numeral 24 whenever the same description applies commonly to both) which have respective fore end portions disposed in confronting relation with the lenses 22L in the illumination windows 21a and 21b. The light guides 24a and 24b are each in the form of a bundle of a multitude of extra fine fiber optics, and, except the respective fore end portions, are assembled together and extended through the insertion rod member 20 and the flexible light guide cable 20c via the control section 20b. The flexible light guide cable 20c is detachably connectible to a light source/ processor assembly unit 25. As shown in FIG. 3, the light source/processor assembly unit 25 is constituted by a light source 25L and a processor 25P. The light source 25L includes an illuminating lamp 26, a concave reflector mirror 27, a condensing lens 28 and a light volume member 29. On the other hand, the endoscope 20 includes in its observation system a solid-state image sensor device 30 which is located at the focus of the objective lens 22L of the observation window 22. A signal cable 31 from the solid-state image sensor device 30 is also extended through the insertion rod member 20a and the flexible light guide cable 20c via the manipulating control section 20b, and disconnectibly connected to the processor 25P of the light source/processor assembly unit 25. Up to this point, the illumination and observation systems of the endoscope are arranged substantially in the same manner as in the prior art counterpart described hereinbefore.

Shown in FIG. 3 are details in construction of the processor 25P of the light source/processor assembly unit 25. In this figure, the reference numeral 32 denotes a video signal processing circuit which reads out accumulated signal charges from the solid-state image sensor device 30 in relation with its exposure and produces video signals by performing known signal processing operations on the read-out signals. In this instance, the solid-state image sensor device 30 is of the type which is operated under the so-called sequential color scan drive to produce sequentially picture signals of R (red), G (green) and B (blue). For this purpose, a rotary color filter 33 is interposed between the condensing lens 28 and the input end of the light guide 24 which is connected to the light source 25L. Output signals of the video signal processing circuit 32 are converted into digital signals through A/D converter 34, and stored in a memory 35. As soon as one frame of picture data are stored in the memory 35, they are simultaneously read out and converted into analog signals through. D/A converters 36R, 36G and 36B to output simultaneous color picture signals to a monitor 38 through an encoder 37.

The output signals of the video signal processing circuit 32 are also fed to ALC circuit 39 which detects the luminance level of output signals of the solid-state image sensor device 30 and, according to variations in luminance level, drives the light volume member 29 by way of an iris drive mechanism 40 to adjust the input light volume of the light guide 24 from the illuminating lamp 26.

According to the invention, a window blockage sensor unit is provided in association with the above-described illumination and observation systems, the window blockage sensor unit being adapted to detect the existence of a blocking obstacle in abnormal nearness of the illumination window 21. The window blockage sensor unit includes a couple of fiber optics bundles 41a and 41b which serve to pick up and feed back light reflections from a blocking obstacle if any, each one of the fiber optics bundles 41a and 41b consisting of a plural number of fiber optics having the respective fore ends disposed within the illumination window 21. The proximal ends of the respective fiber optics bundles 41a and 41b are extended into the manipulating control section 20b on the main body of the endoscope and disposed face to face with light sensitive elements 42a or 42b, respectively. Signals indicative of reflection light levels perceived by the light sensitive elements 42a and 42b are fed to a control circuit 43 thereby to determine whether or not the illumination windows 21a and 21b are in a blocked state. If either the illumination window 21a or 21b is determined to be in a blocked state, the control circuit 43 dispatches a command signal to the iris drive mechanism 40 to adjust the light volume member 29 toward a safe illumination light level while indicating on the viewing screen of the monitor 38 a sign that an illumination window is in a blocked state.

Figure 4:
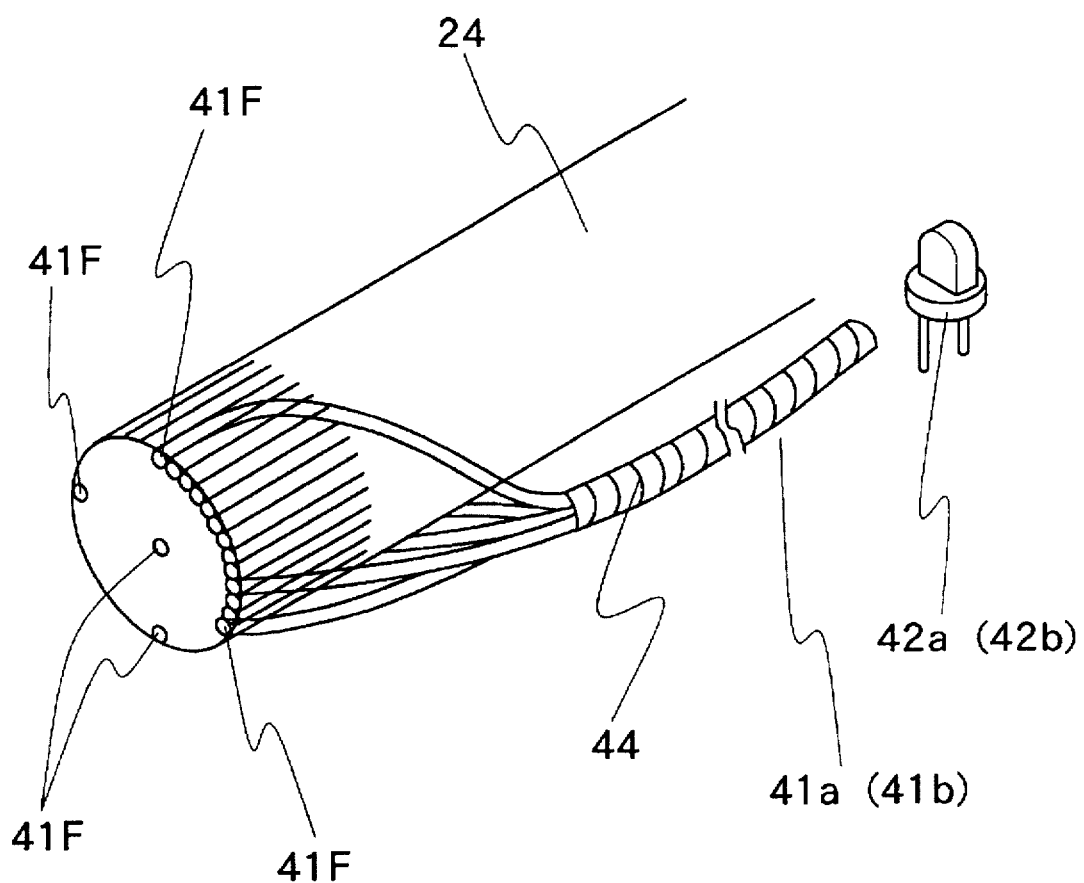
FIG. 4 is a schematic view adopted to show the construction of a window blockage sensor according to the invention.

In the particular embodiment shown, the fiber optics bundles 41a and 41b are each constituted by a set of five fiber optics filaments which are located in five discrete positions at the light-emitting end face of the light guides 24a (or 24b) within the illumination window 21, more specifically, one filament located at a center portion of the light-emitting face at the output end of the light guide and four filaments located in peripheral portions of the light-emitting face at angular intervals of 90° as shown particularly in FIG. 4. The five filaments of the fiber optics 41F in each of the fiber optics bundles 41a and 41b are separated from the light guide 24a or 24b at a position behind the output end of the latter and bundled together by light-shielding taping 44 which forms a light shielding sleeve 44 extending as far as the proximal end of the fiber optics bundle 41a (or 41b) confronting the light sensitive element 42a (or 42b) on the manipulating control section 20b on the main body of the endoscope. The tapings 44 on the fiber optics bundles 41a and 41b serve to shield off the influences of illumination light which is transmitted through the respective light guides.

In use of the endoscope 10 with the above-described arrangements according to the invention, the flexible insertion rod member 20a is introduced into a intracavitary portion of a patient in the usual manner for an examination or for diagnostic purposes. An intracavitary region which is of particular interest in terms of examination or diagnosis is irradiated with the illumination light projected through the illumination window 21 at the distal end of the insertion rod member 20a while the image of the subject is picked up by the solid-state image sensor 30 through the observation window 22. On each exposure, signal charges are accumulated in the solid-state image sensor 30 depending upon the light intensity to which it is exposed. The signal charges accumulated in the solid-state image sensor 30 are transferred to the processor 25P and thereby converted into video signals by known signal processing operations as described hereinbefore to display video images of the subject on the viewing screen of the monitor 38.

In case of an endoscopic examination in an upper digestive system, for example, the intracavitary portion to be examined may be of a tubular shape like an alimentary tract or of a hollow cavity like stomach. When the insertion rod member 20a is introduced into a long open-ended tubular organ, almost no light is reflected back toward the illumination window 21. On the other hand, in case of an examination within a hollow cavity like the stomach and at a position near an intracavitary wall like the gastric wall, it is very likely that the illumination window 21 is located at a close distance from the intracavitary wall, irradiating same with light beams of higher intensity and naturally of greater heat quantity. In this regard, even in an examination at a position near an intracavitary wall, the light rays coming out through the illumination lens 21L are normally diffused to some extent, so that an intracavitary region of interest can be irradiated free of thermal burns or similar troubles for a limited time period as long as the illumination window 21 is kept at a certain distance from the intracavitary wall. However, if the illumination window 21 is brought closer to an intracavitary wall portion, a light spot of a smaller diameter could be impinged in a concentrated manner on a very narrow region before being diffused by the action of the illumination lens 21L, causing thermal burns to the irradiated region within a very short period of time by the heat of intensified illumination light.

In this connection, the illumination windows 21a and 21b are located separately on the opposite sides of the observation window 22, so that there may arise a situation where one of the illumination windows 21a and 21b, for example, one illumination window 21a is blocked by an intracavitary wall while the other illumination window 21b and the observation window 22 are in unblocked state as shown in FIG. 5. In such a situation, because of a drop in illumination light level within the view field of the observation window 22, normally ALC circuit 39 is actuated to send the iris drive circuit 42 a command signal for intensification of the illumination light, namely, a signal for opening the light volume member 29 wider. As a result, the illumination light is fed to the light guide 24 in a greater volume despite further intensification of the light spot impinging on the blocking intracavitary wall.

As the illumination windows 21a and 21b approach an intracavitary wall, however, the illumination light is reflected back more strongly toward the respective illumination windows 21a and 21b. These light reflections from the confronting intracavitary wall are picked up by the fiber optics bundles 41a and 41b and transmitted to the light sensitive elements 42a and 42b, which produce voltaic or other electrical signals according to received reflection light levels for supply to the control circuit 43. On the basis of a preset reference level, the control circuit 43 produces a command signal to be applied to the light volume member 29 should the reflection light level perceived by either the light sensitive element 42a or 42b (the reflection light level perceived by the light sensitive element 42a in case the illumination window 21a is in a blocked state) exceed the preset reference value, thereby to adjust the volume of input light to the light guide 24 to an appropriate illumination level. In this instance, the term "appropriate illumination light level" means a light level at which endoscopic observation of a subject is feasible by way of the images picked up through the observation window 22 without causing thermal burns to the blocking intracavitary wall portion in front of the illumination window or windows. Of course, from the standpoint of preventing thermal burns, the light volume member 29 may be totally shut off upon detection of blockage of an illumination window. However, it could lead to a more dangerous situation since the images of an intracavitary portion under observation are completely blackened out on the viewing screen of the monitor 38.

As described hereinbefore, the volume of input illumination light to the light guide 24 is adjusted upon detection of blockage of an illumination window. At this time, if desired, an alarm sign for possible thermal burns may be simultaneously displayed on the monitor 38. Given such an alarm, the operator of the endoscope can avoid thermal burns or similar damages by relocating the distal end portion of the insertion rod member 10a or by taking other countermeasures.

In case of an endoscope with a couple of illumination windows 21a and 21b as described above, it is necessary for the window blockage sensor means to have a couple of fiber optics bundles for feeding back light reflections separately to a couple of light sensitive elements from the respective illumination windows. However, in case of an endoscope with one illumination window, the window blockage sensor means suffices to have only one set of reflection feedback fiber optics bundle and light sensitive element. The reflection feedback fiber optics bundle can be formed by separating part of fiber optics filaments of the light guide, or by assembling into the light guide a certain number of additional fiber optics filaments which are designed specifically for the reflection feedback. Further, the individual fiber optics filaments in each of the reflection feedback bundles 41a and 41b are located at five discrete positions within the illumination windows 21a and 21b, one filament being located at the center and four filaments being located in peripheral portions at angular intervals of 90° for the purpose of detecting both total and partial blockages of the illumination window 21a or 21b. However, even if the window blockage sensor has the fiber optics only at the center of the illumination window, it can detect a blocked state with relatively high accuracy. Besides, the light sensitive elements 42a and 42b may be mounted on a structure other than the main body 20c of the endoscope, for example, may be mounted in suitable positions within the light source/processor assembly unit 25.

The cause of illumination window blockage can be either an intracavitary wall portion which exists in abnormal nearness to an illumination window or body fluids or other contaminants which cover an illumination window to reflect back the illumination light to such a degree as to cause a distinctive change in the reflection light level as perceived by the light sensitive element through the reflection feedback fiber optics bundle. In case the illumination window is covered with body fluids or similar contaminants, however, the reflection light perceived by the light sensitive element remains at the same level even if the insertion rod member of the endoscope is moved relative to an intracavitary wall. On the other hand, in case of a blockage by an intracavitary wall, even slight movements of the insertion rod member or of a blocking intracavitary wall are responded by variations in the reflection light level perceived by the light sensitive element.

Figure 6:
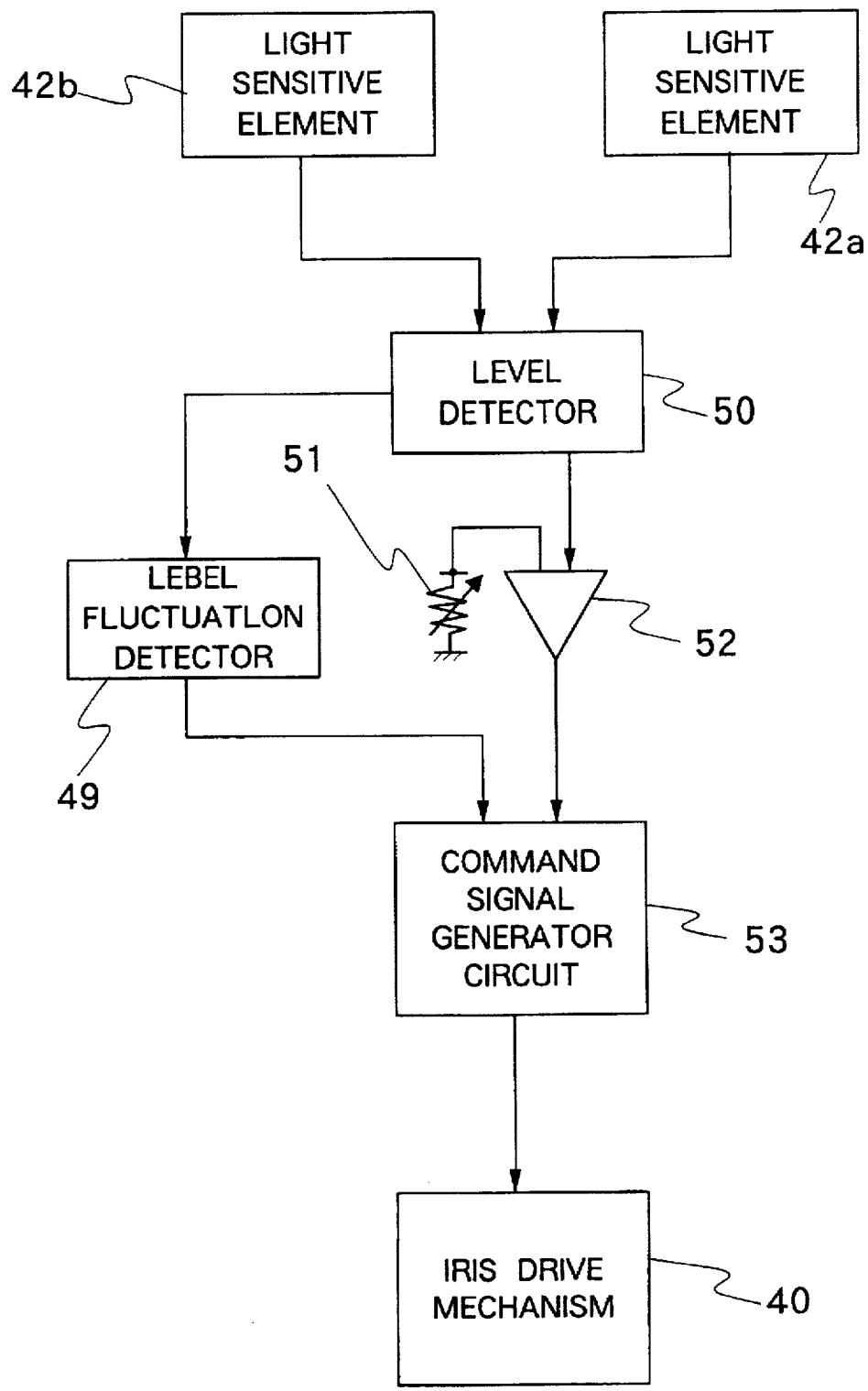
FIG. 6 is a circuit diagram of an illumination light control arranged to detect the cause of window blockage.

In consideration of these phenomena, the control circuit 43 employs a circuit arrangement as shown in FIG. 6, which is capable of distinguishing between light reflections from an intracavitary wall in contact with or in abnormal nearness to the illumination window and light reflections from contaminants covering the surface of the illumination window. More specifically, signals from the light sensitive elements 42a and 42b are fed to a level detector 50 to determine the perceived reflection light levels. Output signal of the level detector 50 is fed to a comparator 52 for comparison with a preset reference value from a reference level setter 51. Therefore, if an output signal of the level detector 50 is of a light level in excess of the reference value, it is determined that either the illumination window 21a or 21b is in a blocked state, sending a window blockage signal to a command signal generator circuit 53. On the other hand, signals from the light sensitive elements 42a and 42b are also fed to a level fluctuation detector 49 which serves to determine the cause of blockage when either the illumination window 21a or 21b is found to be in a blocked state. Namely, when the window blockage is caused by an intracavitary wall which is in contact with or in abnormal nearness to an illumination window, this is detected by way of fluctuations in the received reflection light level resulting from movements of the intracavitary wall itself and/or of the freely movable catheter-like insertion rod member 20a of the endoscope. Relative movements between the insertion rod member 20a of the endoscope and the blocking intracavitary wall cause changes in positions of the illumination windows 21a and 21b relative to the blocking intracavitary wall, varying the reflection light levels perceived by the light sensitive elements 42a and 42b. The variations in the reflection light levels are detected at the level fluctuation detector 49 which incorporates, for example, a differential circuit for this purpose. If it is determined by the light level fluctuation detector 49 that a signal of received reflection light level contains a variation in excess of a predetermined reference value, this signal is sent to the command signal generator circuit 53.

As described above, a blocked state of an illumination window is detected on the basis of a signal from the level detector, and the cause of the blockage is judged on the basis of a signal from the light level fluctuation detector 54. Accordingly, based on these two signals, the command signal generator circuit 53 determines whether or not an illumination window is in a blocked state due to existence of an intracavitary wall in contact with or in abnormal nearness to the illumination window or due to existence of contaminants on the illumination window. In case it is determined that an intracavitary wall is in contact with or in abnormal nearness to an illumination window, a sign of window blockage is indicated, for example, in characters on the screen of the monitor 38, at the same time driving the light volume member to adjust the illumination light to an appropriate level. In case of deposition of contaminants on an illumination window, a corresponding sign is displayed on the monitor 38, urging the operator to wash off contaminants by spouting a washing fluid onto the contaminated window from the washing nozzle 23. Of course, in this case, no adjustment is made of the light volume to be fed to the light guide.

What is claimed is:

1. An endoscope comprising:
   a flexible insertion rod member having a distal end;
   an illumination window provided at the distal end of said insertion rod member;
   a light source which generates illumination light;
   a light guide passed through said insertion rod member for transmitting the illumination light from said light source to said illumination window to illuminate a subject to be observed by the endoscope; and
   a window blockage sensor unit located inside of said illumination window to detect an existence of a blocking obstacle in front of said illumination window by way of light reflections from the blocking obstacle, said window blockage sensor unit comprising
   a reflection light feedback fiber optics member having at least one fiber optics filament extended through said insertion rod member of the endoscope and having one end portion disposed within said illumination window, and
   a light sensitive element located facing to the other end portion of said reflection light feedback fiber optics member to detect a blocked condition at said illumination window on the basis of a change of reflection light level received by said reflection light feedback fiber optics member.

2. An endoscope as defined in claim 1, wherein said reflection light feedback fiber optics member is arranged in said light guide.

3. An endoscope as defined in claim 2, wherein said reflection light feedback fiber optics member is enshrouded in a light shielding material.

4. An endoscope as defined in claim 2, wherein said at least one fiber optics filament is located at a center of said light guide.

5. An endoscope comprising:
   a flexible insertion rod member;
   an illumination window at a distal end of the insertion rod member;
   a light guide passed through the insertion rod member for transmitting illumination light from a light source to the illumination window to illuminate a subject to be observed by the endoscope;
   an illumination light control comprising a window blockage sensor unit to detect an existence of a blocking obstacle in front of the illumination window by way of light reflections from the blocking obstacle, an end of said window blockage sensor unit for receiving the light reflections being positioned in the illumination window; and
   a controller to adjust an amount of light input to the light guide from the light source such that the blocking obstacle is not damaged by the illumination light when said window blockage sensor unit detects the existence of the blocking obstacle.

* * * * *